United States Patent [19]

Bailey

[11] Patent Number: 5,876,203
[45] Date of Patent: Mar. 2, 1999

[54] PERMANENTLY LUBRICATED DENTAL PROPHYLAXIS ANGLE

[75] Inventor: Ronald L. Bailey, Harvester, Mo.

[73] Assignee: Young Dental Manufacturing Company, Earth City, Mo.

[21] Appl. No.: 960,852

[22] Filed: Oct. 30, 1997

Related U.S. Application Data

[63] Continuation of Ser. No. 515,825, Aug. 16, 1995, Pat. No. 5,683,247.

[51] Int. Cl.$^6$ ................................................. A61C 3/00
[52] U.S. Cl. ........................... 433/104; 433/115; 433/125
[58] Field of Search .................................... 433/115, 125, 433/126, 103, 104

[56] References Cited

U.S. PATENT DOCUMENTS

| | | | |
|---|---|---|---|
| 2,098,317 | 11/1937 | Staunt | 433/115 X |
| 3,163,934 | 1/1965 | Wiseman . | |
| 3,407,502 | 10/1968 | Richmond . | |
| 3,478,433 | 4/1968 | Richmond . | |
| 4,182,041 | 1/1980 | Girard | 433/125 X |
| 4,292,027 | 9/1981 | Richmond . | |
| 4,365,956 | 12/1982 | Bailey . | |
| 4,486,175 | 12/1984 | Fisher et al. | 433/115 X |
| 5,062,796 | 11/1991 | Rosenberg | 433/125 X |
| 5,160,263 | 11/1992 | Meller et al. | 433/125 |
| 5,484,284 | 1/1996 | Bailey | 433/125 |
| 5,642,995 | 7/1997 | Bailey | 433/115 |
| 5,683,247 | 11/1997 | Bailey | 433/104 |

OTHER PUBLICATIONS

Young Dental Manufacturing Company, "C–Model Head Ass'y" (6 pages) (1975).

*Primary Examiner*—Jeffrey A. Smith
*Attorney, Agent, or Firm*—Polster, Lieder, Woodruff & Lucchesi

[57] ABSTRACT

A maintenance-free dental prophylaxis angle includes a one-piece body including a sleeve and a head. The sleeve and head define intersecting bores. A drive assembly, comprising a drive gear and a bushing, is force fitted in the sleeve. A one-piece driven gear is received in the head bore to be driven by the drive assembly. The driven gear includes an upper bur tube, a gear part, and a lower shaft. The gear part of the driven gear rests on an upper face of a boss in the head, the boss forming a thrust bearing for the driven gear. Intersecting bores in the boss form part of a lubricant circulating system. A metal cap is force fitted in the head bore to close the head bore and retain the driven gear in place in the head. A dental tool is connected to the bur tube of the driven gear, and forms a seal with the cap.

25 Claims, 4 Drawing Sheets

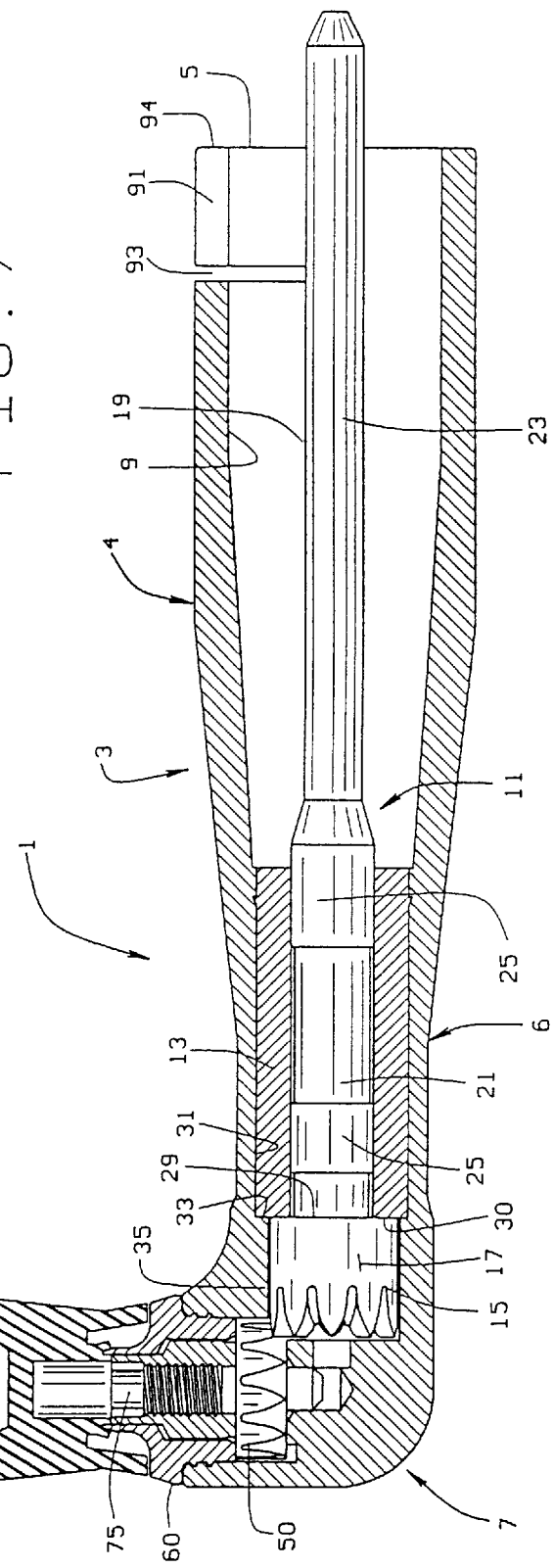
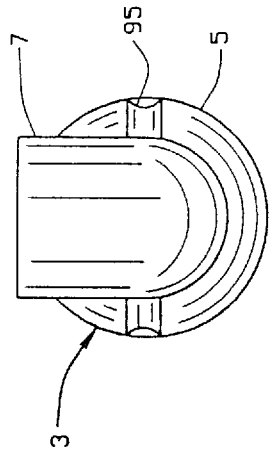
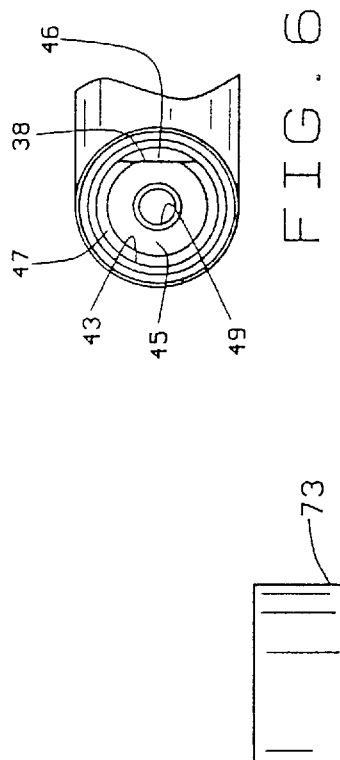

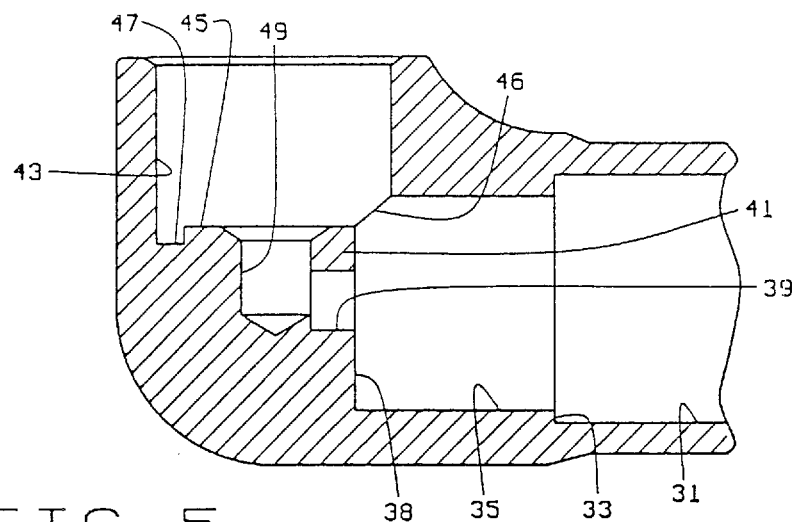
FIG. 5
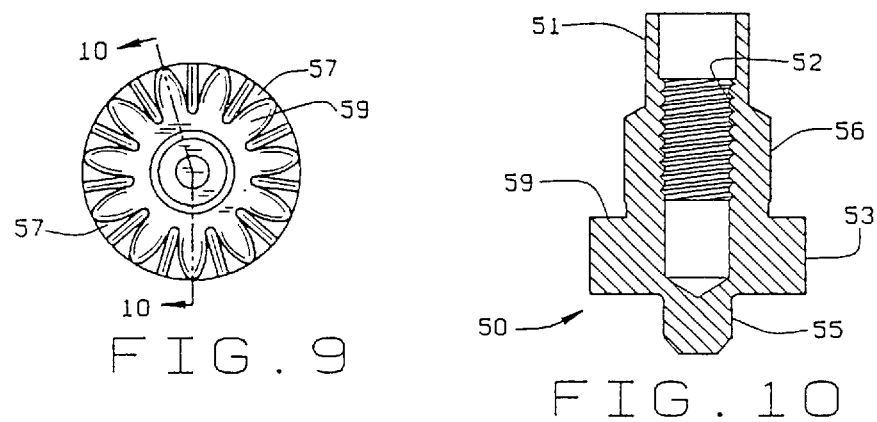
FIG. 9
FIG. 10
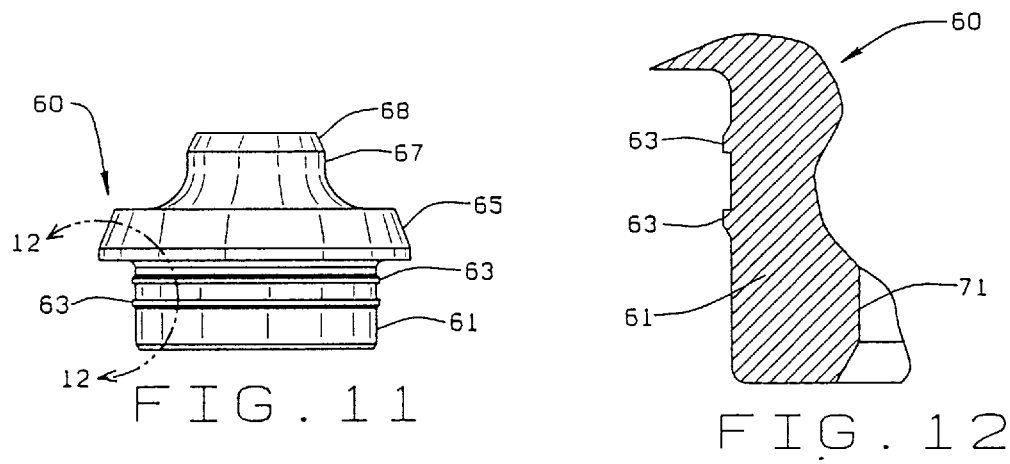
FIG. 11
FIG. 12

PERMANENTLY LUBRICATED DENTAL PROPHYLAXIS ANGLE

CROSS-REFERENCE TO RELATED APPLICATION

This is a continuation of application Ser. No. 08/515,825, filed on Aug. 16, 1995, now U.S. Pat. No. 5,683,247.

BACKGROUND OF THE INVENTION

This invention relates to dental prophylaxis angles (commonly referred to as prophy angles). It has particular application to a prophy angle which need not be lubricated even after repeated autoclave cycles. It also has more general application to making a simple prophy angle with a particularly effective driven gear and thrust bearing for its driven gear.

Prophy angles currently available are either low-cost disposable prophy angles which are discarded after each use or else expensive reusable metal prophy angles which require a considerable amount of care to maintain. A reusable angle must not only be autoclaved between uses or procedures to ensure that the angle is sterile for the next procedure, but it must be maintained. Reusable angles need to be lubricated to run smoothly. The lubrication, however, breaks down and is lost over time through use and because of the autoclaving. Reusable angles must therefore be disassembled periodically to be lubricated. Some manufacturers recommend that prophy angles be lubricated after every ten hours of use. If the angle is not lubricated, the angle will eventually seize up and become inoperable. Through use, debris may also find its way into the angle's head. This debris can interfere with the operation of the angle's gears, and can ultimately ruin the gears. The angle must therefore also be cleaned periodically, to remove any debris, such as grit, which may have found its way into the angle. Many dentists and hygienists do not lubricate and clean their prophy angles on a regular schedule. If the angles are not lubricated and cleaned periodically, they will eventually fail.

An example of an expensive, high-quality reusable prophy angle is the TS2™ angle sold by Young Dental Manufacturing Company of Earth City, Mo. This angle is shown in FIG. 1. All of the parts are machined from bronze and stainless steel. A body B terminates in an externally threaded stud B1. A drive gear member D includes a shaft DS rotatably mounted in an axial bore of the body and a drive gear DG butted against the end of the stud B1. A head part H is threaded onto the stud B1. The head part includes an axial bore HB and a bore extension HE. A post P is press fitted into the bore extension HE. The post P acts as a thrust bearing for a driven gear Dn. The driven gear Dn includes a gear part DnG and an upwardly-extending internally threaded bur tube DnT. A cap C is threaded into the open end of the head bore and forms radial bearings for the driven gear. A stem CS on the outside of the cap terminates in an externally beveled knife edge, a short distance above the top of the bur tube. Specially designed dental tools, such as prophy cups manufactured by Young Dental Manufacturing Company, when they are screwed into the bur tube DnT, form a seal with the stem CS and prevent intrusion of material from the patient's mouth into the angle. One manner of forming the seal is described in my U.S. Pat. No. 5,484,284.

An alternative to single-use disposable prophy angles and expensive reusable angles has been proposed in Wiseman, U.S. Pat. No. 3,163,934. That patent discloses a relatively low-cost prophy angle whose body, cap, and drive shaft bearing are made of polypropylene, and whose drive gear, driven gear, bearing-locking collar, and ball thrust bearing are made of metal. A small quantity of silicone lubricant is packed into the head (nose) of the angle. Although this angle is designed to be sealed and to be repeatedly sterilized, it is not sufficiently sealed to prevent intrusion of materials from the patient's mouth or leakage of lubricant during use, and it does not lend itself to repeated autoclaving. Moreover, its construction does not lend itself to precise alignment of the moving parts, thereby increasing the difficulty of making the instrument run smoothly, quietly, and reliably. The construction requires seven separate parts and relatively complicated assembly.

SUMMARY OF THE INVENTION

One object of the present invention is to provide a dental prophy angle which need not be lubricated or cleaned of debris during a long useful life.

Another object is to provide such an angle which includes an effective means for sealing the angle during use.

Another object is to provide such an angle which may be produced so inexpensively that it may be economically replaced after a period of time, such as one year.

Another object is to provide such an angle which provides an accurate, simple mounting for its driven gear.

Other objects will become apparent to those skilled in the art in light of the following disclosure and accompanying drawings.

In accordance with one aspect of the invention, generally stated, a maintenance-free dental prophylaxis angle is provided which includes a one-piece body including a sleeve and a head. The sleeve and head define intersecting bores. A drive assembly, comprising a drive gear and a bushing, is force fitted into the sleeve, against a rearwardly facing shoulder. The drive gear includes a gear part and a smaller shaft part which extends rearwardly through the bushing and body sleeve. The shaft extends slightly beyond the rear end of the prophy angle to be grasped by the collet of a dental handpiece, such as the Doriot nose of an air motor handpiece. A driven gear is received in the head bore to be driven by the drive gear. The driven gear includes an upper shaft or bur tube, a gear part, and a lower shaft, all machined from one piece of metal. The lower shaft is made sufficiently short to permit machining of gear teeth on the gear part, preferably shorter than the axial height of the gear part.

In accordance with another aspect of the invention, the gear part of the driven gear rests on the upper surface of a boss in the head, the boss forming a thrust bearing for the driven gear. Preferably, an arcuate groove is provided in the upper surface of the boss to prevent the tips of the gear teeth from wearing down the thrust bearing surface.

A metal cap is mounted, preferably force fitted, in the head bore to close the head bore and retain the driven gear in place in the head. A dental tool such as a prophylaxis cup is connected to the bur tube of the driven gear, and an elastomeric portion of the tool forms a seal with the cap. Preferably, the cap includes a hollow stem surrounding the bur tube, and a knife edge on the hollow stem cuts into an elastomeric ring on the dental tool, in accordance with my previously mentioned U.S. Pat. No. 5,484,284. The cap forms a tight fit with the body. The seal between the dental tool and the cap substantially prevents foreign material from entering the body and reduces or eliminates the need to clean the interior of the prophy angle.

The drive gear preferably includes a gear part and a shaft part machined from a single piece. The gear part is larger than the shaft part and is trapped between a forward end of the bushing and a side face of the boss in the head of the angle body to limit axial movement to a few thousandths of an inch.

The boss in the head includes a head bore extension which extends substantially beneath the end of the lower shaft of the driven gear and which acts as a lubricant reservoir. An aperture in the side wall of the boss communicates with the head bore extension and permits lubricant to circulate between a chamber housing the drive gear part and a chamber housing the driven gear part. A lubricant which can withstand many autoclaving cycles, such as a lithium grease, is preferably used. The angle thus does not have to be lubricated during its useful life.

Preferably, the angle cannot easily be disassembled, and can be used for an extended period of time, for example one year, without requiring any maintenance. Because the construction permits the angle to be produced at low cost, at the end of its useful life the angle can be replaced with a new angle.

BRIEF DESCRIPTION OF THE DRAWINGS

FIG. 2 is a cross-sectional view of a dental prophy angle of the present invention;

FIG. 5 is a cross-sectional view of a head portion of the body of the angle;

FIG. 6 is a top plan view of the head portion of the body of the angle;

FIG. 7 is a view in front end elevation of the body of the angle;

FIG. 9 is an end view of a driven gear of the angle;

FIG. 10 is a sectional view of the driven gear of FIG. 9, taken along the line 10—10;

FIG. 11 is a view in side elevation of the cap of the angle; and

FIG. 12 is a detail of the cap of FIG. 11, as indicated at 12—12 of FIG. 11.

DESCRIPTION OF THE PREFERRED EMBODIMENT

Figure 1:
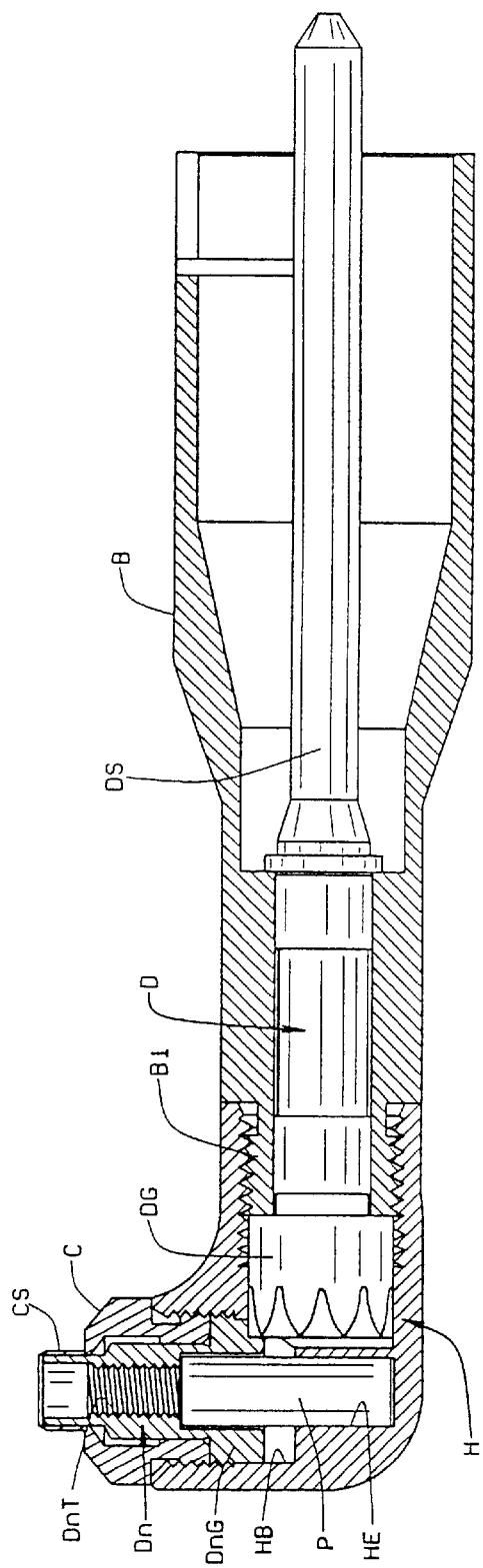
FIG. 1 is a cross-sectional view of a prior art TS2 dental prophy angle.

Referring now to the drawings, and in particular to FIG. 2, reference numeral 1 indicates a preferred embodiment of a dental prophy angle of the present invention. Angle 1 includes a one-piece metal body 3 having a sleeve 4 with an open back end 5, a neck 6, and a head 7.

Sleeve 4 and neck 6 define an axially extending body bore 9 which receives a drive assembly 11. Drive assembly 11 includes a bushing 13 and a drive gear 15. The bushing preferably is formed as a cylinder which receives drive gear 15. Drive gear 15 includes a drive gear part 17 and a rearwardly extending shaft 19. Shaft 19 is sufficiently long to be received by a handpiece, such as a Doriot type handpiece. Shaft 19 has a forward section 21 and a rear section 23, having a narrower diameter than the forward section. The forward section 21 extends back from the drive gear part 17 through the bushing 13. The forward shaft section 21 includes two spaced apart sections 25 of increased diameter which define bearing surfaces for the drive assembly and a central portion which is smaller in diameter. One of the sections 25 of shaft 19 extends slightly rearwardly of bushing 13. The back surface 29 of gear part 17 has a diameter larger than the inner diameter of bushing 13, and abuts the front surface 30 of the bushing 13. The surface 30 thus acts as a thrust bearing.

Bore 9 includes a reduced diameter section 31 in neck 6 in which bushing 13 is received. A yet smaller diameter section 35 at the forward end of bore section 31 defines a rearwardly facing shoulder 33 against which the forward face 30 of the bushing 13 abuts. The forward end of the body bore section 35 is defined by a vertical face 38 of a boss 41. A body bore extension 39 is provided through face 38 for purposes set out hereinbelow.

Drive gear part 17 is received in bore section 35. Bushing 13 is force fit in neck bore 31 to frictionally maintain the bushing, and hence the drive assembly 11, in place in body 3. The bushing 13 includes an annular barb 37 at the back thereof. The barb 37 extends about 0.002" to about 0.004" beyond the outer face of the bushing, to prevent removal of the drive assembly from angle body 3 after the bushing 13 is force fitted into the neck bore 31 as described hereinafter. By way of example, the bushing 13 may have a nominal diameter of 0.227", the annular barb 37 a nominal diameter of 0.232", and the neck bore a nominal diameter of 0.229". The drive gear part 17 is thus constrained against axial movement of more than a few thousandths of an inch by the front face 30 of the bushing 13 and the rear face 38 of the boss 41.

Figure 3:
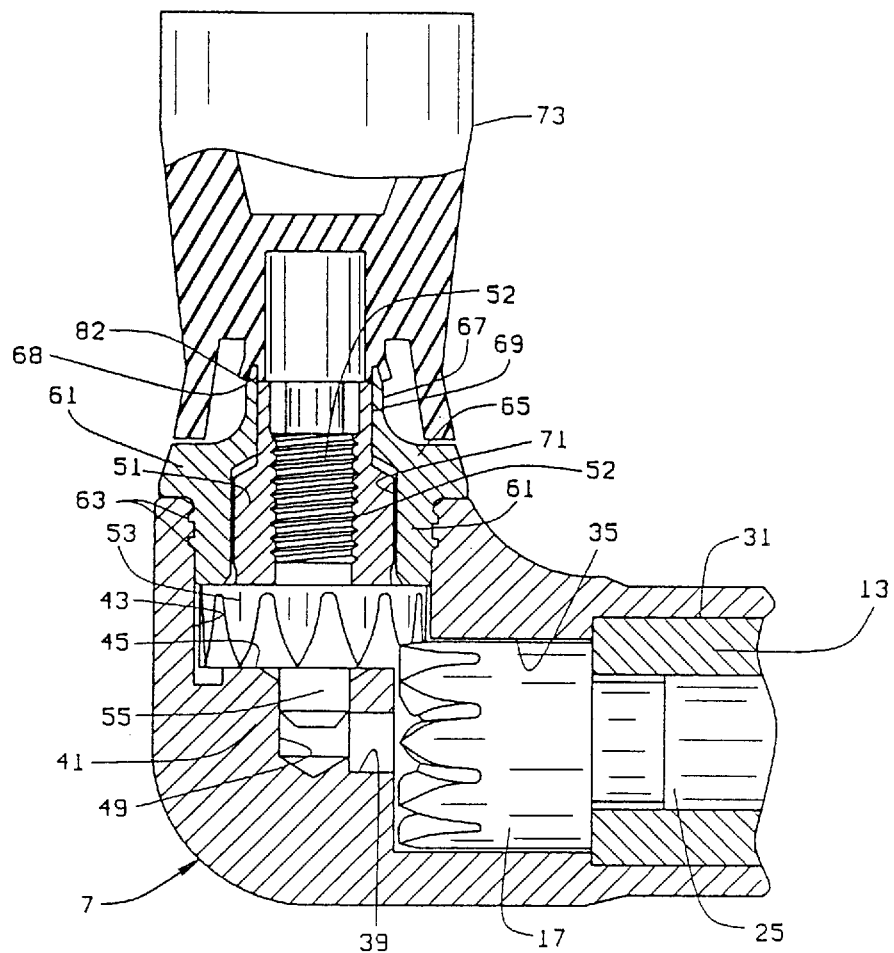
FIG. 3 is an enlarged view of a head and cap assembly of the prophy angle.
Figure 4:
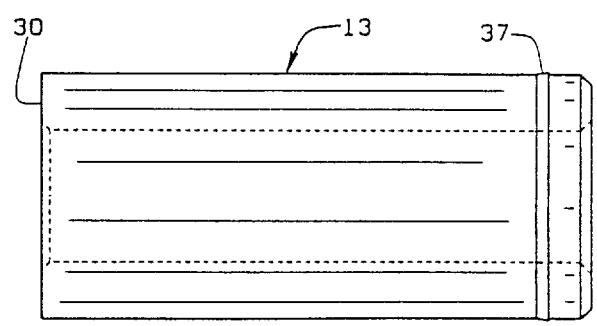
FIG. 4 is an view of a bushing part of the prophy angle.

Head 7 is shown in more detail in FIGS. 3–5. Head 7 is formed integrally with sleeve 4 and includes boss 41 and an upwardly opening bore 43 which defines an upper face 45 of the boss 41. Bore 43 intersects the forward portion 35 of sleeve bore 9 in a segment 46 at the rear of head bore 43 above the upper face 45 of boss 41. An arcuate groove 47 extends around the periphery of the upper face 45 of the boss 41. A head bore extension 49 extends through the upper face 45 of the boss 41 and intersects the body bore extension 39.

Head bore 43 receives a driven gear 50. The driven gear 50 includes an upper shaft or bur tube 51, a gear part 53, and a lower stub shaft 55, all machined from one piece of metal. The bur tube 51 is bored and threaded as at 52. The lower stub shaft 55 is made sufficiently short to permit machining of gear teeth 57 on the lower side of the gear part 53, as shown in FIGS. 3 and 10, without damaging the stub shaft 55. The stub shaft 55 is shorter than the axial height of the gear part 53. It will be seen that the gear teeth 57 are cut in the form of bevel gears to provide smooth engagement and rotation with similar gear teeth of the drive gear part 17. The stub shaft 55 is received in bore extension 49 to rotatably mount driven gear 50 in head 7. The lower face 59 of gear part 53 rests on the upper face 45 of boss 41. Arcuate groove 47 is aligned with and clears the ends of gear teeth 57 and prevents damage to the upper face 45 of boss 41 as the angle is used. Without the groove 47, slight eccentricities in the rotation of the driven gear 59 can cause the gear teeth 57 to come into contact with and degrade the boss surface 47.

A cap 60 (shown in detail in FIGS. 3, 11 and 12) is received in head bore 43 to secure gear 50 in the bore and to prevent axial movement of gear 50 relative to head 7. Cap 60 includes a trunk 61 which is force fit into cavity 43. Trunk 61 includes barbs 63 to prevent the cap from being removed from the cavity. By way of example, the trunk 61 may have a nominal diameter of 0.214", the annular barbs 63 a nominal diameter of 0.218", and the head bore a nominal diameter of 0.216". An annular flange 65 extends radially outwardly from trunk 61 over the top surface of head 7. The distance from the bottom of flange 65 to the bottom of trunk 61 is controlled to provide a clearance of less than a few thousandths of an inch between the bottom of the trunk 61 and the top of gear part 53. A stem 67 extends upwardly from flange 65. Stem 67 is concentric with, but of a smaller outer diameter than, trunk 61. The upper end of stem 67 is beveled as at 68 to provide a sharp edge.

Trunk 61 and stem 67 have an axial bore 69 which extends therethrough and which is coaxially aligned with head bore 43. Bur tube 51 of gear 50 extends up through bore 69 to near the top of stem 67. Bur tube 51 has an outer diameter slightly less than bore 69 so that bur tube 51 may rotate in bore 69. To reduce the friction produced by the rotation of bur tube 51 in bore 69, bore 69 is counter-bored, as at 71, to space a wall 56 of bur tube 51 from counterbore 71. As can be appreciated, cap bore 69 and head bore 49 provide bearing means for the driven gear 50.

As shown in FIG. 3, a prophy cup 73, or other dental tool, is screwed into threaded bore 52 of bur tube 51 to be rotated by the driven gear 50 when the driven gear is rotated by the drive gear. Cup 73 has a screw 75 which extends downwardly from the base of the cup, to threadedly secure the cup to the gear boss. Knife edge 68 cuts into an annular bottom surface 82 of cup 73 to form a seal with the cup, as described in U.S. Pat. No. 5,484,284. Preferably, the cup 73 is the cup disclosed in that application.

Preferably, the body of the angle 1 is formed of chrome plated brass, the gears of 303 stainless steel, and the bushing and cap of 440se stainless steel.

Angle 1 is assembled by inserting the drive gear 15 into the bushing 13 to form the drive assembly 11. The drive assembly 11 is then inserted in angle body 3 by passing it through the back 5 of sleeve 4. The assembly 11 is pressed into the neck 31 until the front surface 30 of bushing 13 contacts the shoulder 33 in sleeve neck 31. The annular barb 37 on bushing 13 displaces enough material in the inside of the neck bore 31 to lock the bushing from any axial movement, even when subjected to substantial rearward pull on the shaft 23. The driven gear 50 is then placed in head bore 43 to mesh with drive gear 17. The cap 55 is then placed on head 7 by pressing cap trunk 61 into head bore 43 until the bottom of the cap's flange 65 seats against the top face of the head 7. This secures driven gear 47 in head bore 43. The annular barbs 63 displace enough material in the inside of the head bore 43 to lock the cap from any axial movement. Finally, the dental tool, such as prophy cup 73, is threaded into driven gear bur tube 67.

Because the angle cannot be disassembled, prior to assembly of the angle the bearings and gears are lubricated. The lubricant is preferably a lithium based grease which blends with the molecular structure of the metal components of the angle and does not wear down as readily as other lubricants. The head bore extension 49 extends substantially beneath the end of the lower shaft of the driven gear and acts as a lubricant reservoir as does the body bore extension 39 which communicates with it. The groove 47 also acts as a reservoir for lubricant. The bore extensions 39 and 49 permit lubricant to circulate between the chamber 35 housing the drive gear part and the chamber 43 housing the driven gear part. It has been found that if the angle 1 is operated without the cup 73, lubricant is forced out of the top of the stem 67, thereby indicating that lubricant is circulating when the angle 1 is operated. The angle thus does not have to be lubricated during its useful life.

The seal between the cap and the cup prevents foreign material, which could damage the gears, from entering the body. The angle 1 can therefore be used for a considerable period of time without requiring any maintenance from the dentist or hygienist. The fact that the body is molded or cast as a single piece reduces the number of joints in the angle and thus facilitates the reduction in the possibility of foreign matter entering the angle.

Because the angle body is molded, cast, or machined as a single piece, manufacture and assembly of the angle 1 is less expensive than assembly of multi-piece bodies. Further, because the cap 60 and bushing 13 are force fit into the body, rather than being threaded into the body, as is currently done, mating threads on the cap and bushing, and in the body do not have to be formed. This further reduces the cost of manufacturing the angle. Because the angle does not have to be maintained, unlike current metal angles, and because it is less expensive to produce and manufacture than current metal angles, after a period of time, for example one year, the angle 1 can be replaced with a new angle.

Figure 8:
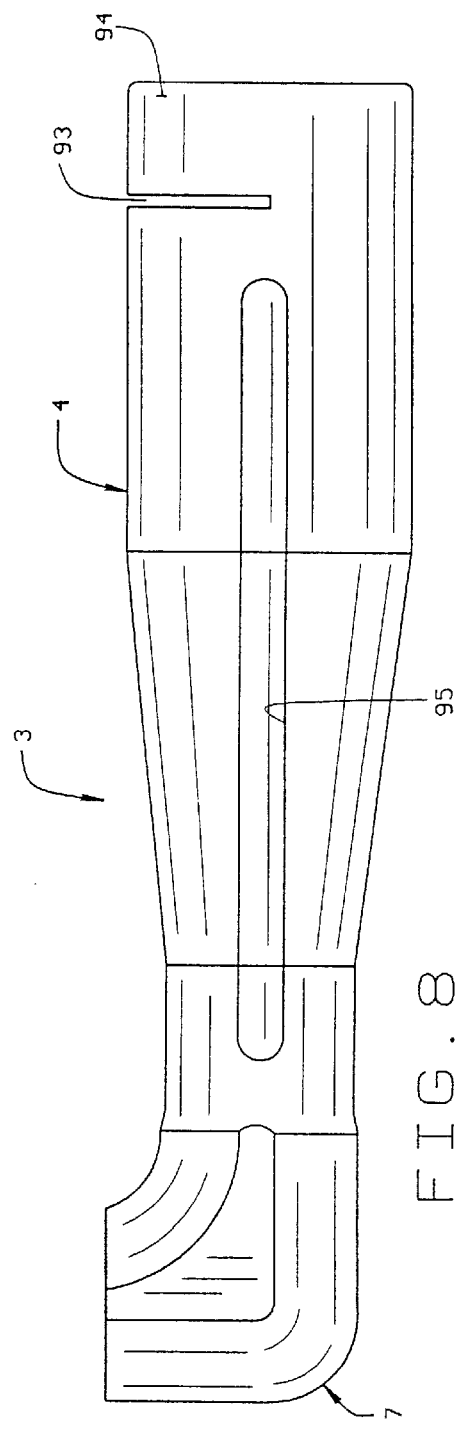
FIG. 8 is a view in side elevation of the body of the angle.

Referring to FIGS. 2, 7 and 8, the sleeve 4 has a locating slot 91 extending axially a short distance from the back edge of body 3. A slit 93 is cut into the sleeve at the end of locating slot 91 to be generally perpendicular to slot 91 and generally parallel to the plane of the back 5 of the angle. The slit 93 creates two spring fingers 94 which expand slightly when the angle is placed on a handpiece. This creates a size-on-size frictional fit with the nose of the handpiece and to hold the angle body angularly and axially with respect to the handpiece independently of the shaft being held by the handpiece chuck, as is standard in the art. The body is provided with two shallow axially extending linear depressions 95 which give the user better rotational control of the angle 1, but which permit easy cleaning of the surface of the body 3.

The foregoing description is set forth only for illustrative purposes and is not meant to be limiting. Numerous variations within the scope of the appended claims will be apparent to those skilled in the art. For example, the bore in the head of the body may be internally threaded and the cap externally threaded to provide a prophy angle in which the cap can be removed for cleaning and lubricating the driven gear and its chamber. The body may be formed of a suitable plastic which can withstand repeated autoclave cycles, as can the drive gear. Preferably, the cap and the driven gear are formed of materials which can retain the sharpness of the edge of the stem and the critical axial dimension and internal threading of the bur tube. The cap may be provided with a protective wall around its hollow stem, as described in my U.S. Pat. No. 5,642,995. Although the dental tool 73 was described to be a prophy cup, other tools, such as brushes, could be used, as long as they have an elastomeric base part which can form a seal with the stem of the cap. Other seals between the cap and dental tool, such as the seal of FIGS. 1–6 of Richmond, U.S. Pat. No. 3,407,502, may be used, although the preferred seal has been found to provide a particularly long-lasting and positive seal. These examples are merely illustrative.

I claim:

1. A dental prophylaxis angle comprising a body including a sleeve and a head defining intersecting bores, a drive gear rotatably mounted in the sleeve and a machined driven gear rotatably mounted in the head bore to be driven by the drive gear, the driven gear including an upper bur tube, a gear part, and a lower stub shaft, formed from a single piece of metal, the gear part being between the upper bur tube and the lower stub shafts the gear part having a lower side adjacent the stub shaft and having teeth facing the lower stub shaft formed in the lower side of the gear part, the lower stub shaft being shorter than the axial height of the gear part and sufficiently short to permit machining of the gear teeth in the lower side of the gear part without damaging the lower stub shaft.

2. The angle of claim 1 wherein the gear part is trapped between a cap and a boss in the angle body to limit axial movement of the driven gear.

3. The angle of claim 1 wherein the gear part has a substantially planar upper surface, the lower side of the gear part being substantially parallel to the upper surface.

4. The angle of claim 1 wherein the stub shaft has a diameter smaller than a diameter of the upper bur tube.

5. A dental prophylaxis angle comprising:

a body including a sleeve and a head defining intersecting bores, a cap mounted in the head bore, a drive gear rotatably mounted in the sleeve, a machined driven gear rotatably mounted in the head bore to be driven by the drive gear, the driven gear including an upper bur tube and a gear part machined from a single piece of metal, the bur tube being rotatably mounted in the cap, the gear part having an upper surface and a lower surface, the upper and lower surfaces being substantially parallel, and a plurality of teeth machined in the lower surface, the teeth facing away from the upper bur tube, the upper surface of the gear part being adjacent a first restraining surface of the cap and the lower surface of the gear part being adjacent a second restraining surface in the head of the body, the gear part being thus trapped between the cap and the second restraining surface to limit axial movement of the driven gear, and a lubricant reservoir formed in the head below the second restraining surface, the lubricant reservoir communicating with the sleeve bore and with the head bore to lubricate both the drive gear and the driven gear.

6. The angle of claim 5 wherein the second restraining surface is an upper surface of a boss machined in the angle body.

7. The angle of claim 6 wherein the upper face of the boss includes an arcuate groove.

8. The angle of claim 5 wherein the sleeve defines a neck portion adjacent the head, the drive gear being received in the neck portion.

9. The angle of claim 5 wherein the cap is force fit in the body to seal the body.

10. The angle of claim 5 wherein the cap includes a knife edge surrounding the bur tube.

11. The angle of claim 5 wherein the drive gear and driven gear are lubricated with a long lasting lubricant which can withstand repeated autoclavings without wearing down for an extended period of time.

12. The angle of claim 5 wherein the cap is made of metal and is force fitted in the head bore to close the head bore and retain the driven gear in place in the head.

13. The angle of claim 5 wherein a dental tool is operatively connected to the driven gear, the dental tool forming a seal with the cap.

14. A dental prophylaxis angle comprising:

a one-piece body including a sleeve and a head defining intersecting bores, the head bore opening upwardly, a cap mounted in the head bore, the cap having an opening therein, a drive gear rotatably mounted in the sleeve, a driven gear rotatably mounted in the head bore to be driven by the drive gear, the driven gear including an upper bur tube and a gear part, the bur tube being rotatably mounted in the cap and communicating with the opening in the cap to permit mounting a dental tool in the bur tube through the opening, the gear part having an upper surface and a lower surface, the upper and lower surfaces being substantially parallel, a restraining surface on the cap adjacent the upper surface of the gear part and a restraining element in the body adjacent the lower surface of the gear part, the gear part being thus trapped between the cap and the restraining element to limit axial movement of the driven gear.

15. The angle of claim 14 wherein the cap is force fit in the head bore to seal the body.

16. The angle of claim 14 wherein the cap includes a knife edge surrounding the opening.

17. The angle of claim 14 wherein the drive gear and driven gear are lubricated with a long lasting lubricant which can withstand repeated autoclavings without wearing down for an extended period of time.

18. The angle of claim 14 wherein the cap is made of metal and is force fitted in the head bore to close the head bore and retain the driven gear in place in the head.

19. The angle of claim 18 wherein the cap includes a shoulder, the shoulder abutting an upper surface of the head.

20. The angle of claim 14 wherein a dental tool is operatively connected to the driven gear, the dental tool forming a seal with the cap.

21. The angle of claim 14 wherein the restraining element is a boss machined in the angle body.

22. The angle of claim 21 wherein the upper face of the boss includes an arcuate groove.

23. The angle of claim 14 wherein the sleeve defines a neck portion adjacent the head, the drive gear being received in the neck portion.

24. The angle of claim 14 wherein the cap includes a knife edge surrounding the opening and wherein a dental tool is operatively connected to the driven gear, the dental tool forming a seal with the knife edge.

25. A dental prophylaxis angle comprising a body including a sleeve and a head defining intersecting bores, a drive gear rotatably mounted in the sleeve and a machined driven gear rotatably mounted in the head bore to be driven by the drive gear, the driven gear including an upper bur tube, a gear part, and a lower stub shaft, formed from a single piece of metal, the gear part being between the upper bur tube and the lower stub shaft and having teeth facing the lower stub shaft, the upper bur tube having a central blind bore to receive a prophylaxis tool shaft, the blind bore terminating above the lower stub shaft, the lower stub shaft being shorter than the axial height of the gear part and sufficiently short to permit machining of the gear teeth in the lower side of the gear part without damaging the lower stub shaft.

\* \* \* \* \*